United States Patent [19]
Craner

[11] Patent Number: 5,590,421
[45] Date of Patent: Jan. 7, 1997

[54] DEVICE AND METHOD FOR TREATMENT OF HAND INVOLVED HABITS

[76] Inventor: James Craner, 395 Tenaya La., P.O. Box 1161, Verdi, Nev. 89439

[21] Appl. No.: 459,540

[22] Filed: Jun. 2, 1995

Related U.S. Application Data

[63] Continuation of Ser. No. 124,103, Sep. 20, 1993, abandoned.

[51] Int. Cl.⁶ ............................... A61F 5/37; A41D 19/00
[52] U.S. Cl. ............................... 2/161.7; 2/163; 128/880; 131/270
[58] Field of Search ........................... 2/159, 160, 161.1, 2/161.7, 163, 16, 19, 20; 128/878, 879, 880; 131/270; 482/44, 47, 48, 49

[56] References Cited

U.S. PATENT DOCUMENTS

| | | | |
|---|---|---|---|
| 2,546,118 | 3/1951 | Wright | 128/879 X |
| 3,533,405 | 10/1970 | Collins | 482/48 X |
| 3,736,926 | 6/1973 | Irby | 128/879 |
| 3,789,840 | 2/1974 | Rosenblatt . | |
| 3,885,576 | 5/1975 | Symmes . | |
| 3,944,220 | 3/1976 | Fasano | 482/47 |
| 4,068,672 | 1/1978 | Guerra . | |
| 4,246,913 | 1/1981 | Ogden et al. . | |
| 4,557,279 | 12/1985 | Fuerste . | |
| 4,746,313 | 5/1988 | Bray et al. | 441/57 |
| 4,747,417 | 5/1988 | Beskin . | |
| 4,768,232 | 9/1988 | Villalobos | 2/19 |
| 4,774,971 | 10/1988 | Vieten . | |
| 4,821,745 | 4/1989 | Rosen et al. . | |
| 4,877,041 | 10/1989 | Barnhouse . | |
| 4,887,181 | 12/1989 | Lenz . | |
| 4,907,605 | 3/1990 | Ray et al. . | |
| 4,911,181 | 3/1990 | Vromen et al. . | |
| 4,920,989 | 5/1990 | Rose et al. . | |
| 4,951,691 | 8/1990 | Leary . | |
| 4,953,572 | 9/1990 | Rose et al. . | |
| 5,042,510 | 8/1991 | Curtiss et al. . | |
| 5,113,530 | 5/1992 | Smith | 2/19 |
| 5,367,711 | 11/1994 | Calagui | 2/163 X |

FOREIGN PATENT DOCUMENTS

| | | | |
|---|---|---|---|
| 2045386 | 12/1992 | Canada | 131/270 |
| 0931199 | 5/1982 | U.S.S.R. | 482/49 |

*Primary Examiner*—Peter Nerbun
*Attorney, Agent, or Firm*—Barry Dale Cash

[57] ABSTRACT

A device and method for treating hand-involved habits, including smoking, hair-twirling, nose-picking, nail-biting, skin-pulling, and the like, is disclosed. The invention consists of a form-fitting barrier placed on the hand of a patient. The barrier is made of a fabric which is generally form fitting and moves with the hand on which it is placed. The barrier is preferably in the form of a glove wherein the second and third digits are substantially inseparably joined together and webbing connects the third and fourth digits and the fourth and fifth digits. An insert portion of the barrier reduces ease of contact between the connected second and third digits and the thumb.

20 Claims, 4 Drawing Sheets

FIG. 3
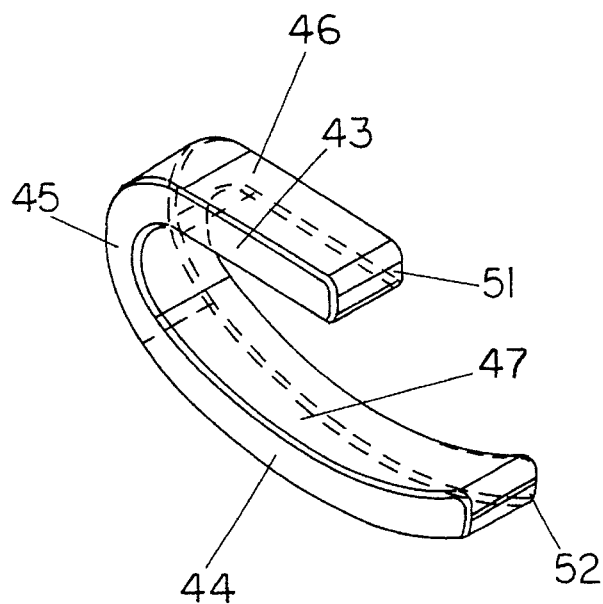
FIG. 5
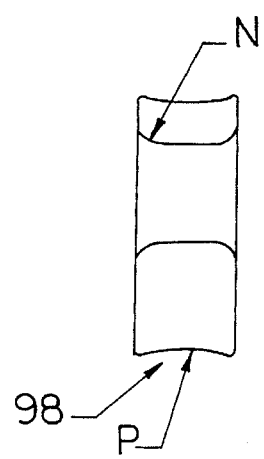
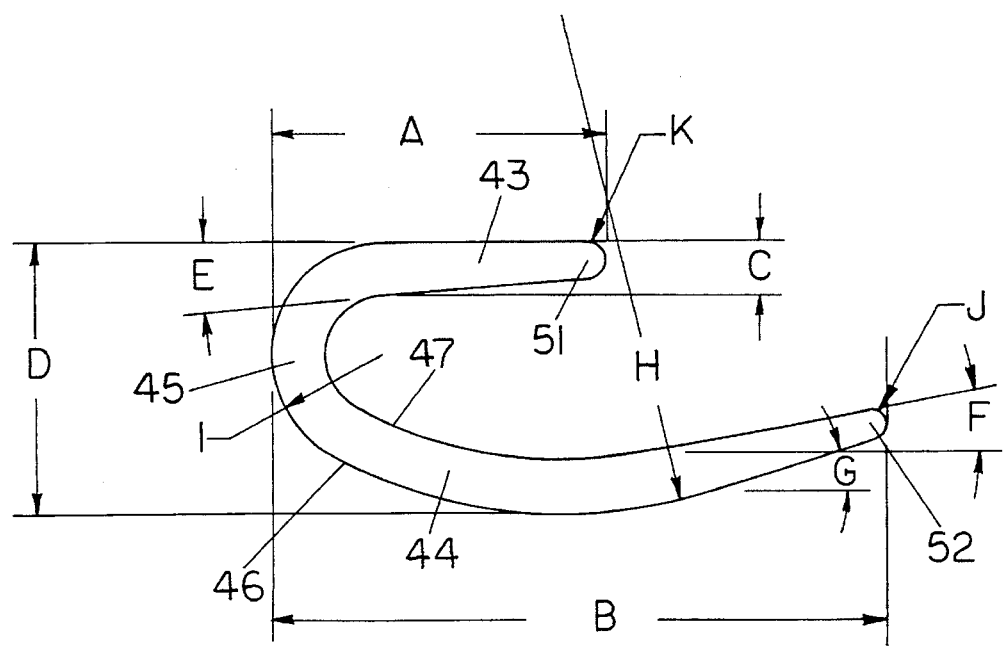
FIG. 4

DEVICE AND METHOD FOR TREATMENT OF HAND INVOLVED HABITS

This application is a continuation of application Ser. No. 08/124,103, filed Sep. 20, 1993, now abandoned.

FIELD OF THE INVENTION

This invention relates to a device and method for cessation of hand-involved habits. In particular, this invention is utilized to aid in smoking cessation.

BACKGROUND OF THE INVENTION

Hand-involved habits, most notably smoking, hair-twirling, nose-picking, nail-biting, skin-pulling and scratching, induce in the practicer a subconscious sense of pleasure, not only through some sense of relief, but also from the actual hand-article contact experienced during the behavior. For example, to a smoker the act of lighting, holding, and manipulating a cigarette is responsible for much of the perceived satisfaction and pleasure that the smoking habit brings to many smokers. These actions often become subconsciously associated with, and thus reinforce, the smoking behavior. It has been repeatedly demonstrated that, without adequate behavioral support methods (to address craving) smokers are unlikely to successfully (permanently) quit. Indeed, for smokers trying to break the habit, the psychological components of craving often greatly exceed the 1–2 weeks of symptoms associated with nicotine withdrawal.

Similarly, the act of touching the hair or nose with the hands, or of placing the fingers in the mouth becomes a source of perceived satisfaction or relief. When an individual attempts to quit the habit, craving lasts from weeks to many months or more. For the other hand-involved habits besides smoking there is no chemical dependency, only the tactile sensations are involved.

When studying the hand involvement in smoking, in particular, it is often observed that most smokers hold a cigarette either between the pointer and middle fingers at any one of various points between the proximal and distal interphalangeal joints (PIP, DIP); between the flexed, adducted thumb and the adjacent pointer finger ("pulp pinch"); or between the thumb, pointer and middle fingers ("three-point pinch"). Contact between the thumb and pointer and/or middle fingers is referred to herein as "opposition." Most smokers prefer to hold the cigarette in the dominant hand.

Established smoking cessation instruments or methods have involved nicotine replacement (gums, patches) and various behavioral methods to deter or reduce smoking behavior. The latter group has typically involved adaptations of a cigarette or cigarette substitute, or orchestrated cues to increase the interval between cigarettes.

OBJECTS OF THE INVENTION

It is accordingly an object of the invention to provide a behavioral device and method designed to interrupt or deter the automatic behavior of lighting up and manipulating a cigarette, enabling the individual to consciously suppress the urge to smoke.

A further object of the invention is to provide a device and method for cessation of other hand-involved habits such as hair twirling, nose-picking, nail-biting, skin-pulling and scratching.

Other objects and advantages of the invention will become apparent to those skilled in the art from the drawings and the following description.

SUMMARY OF THE INVENTION

The invention consists of form-fitting barrier placed on the hand of a patient. The barrier is made of a fabric which is generally form-fitting and moves with the hand on which it is placed. The barrier is preferably in the form of a glove wherein the second and third digits (fingers) are substantially inseparably joined together and webbing connects the third and fourth digits (fingers) and the fourth and fifth digits. An insert portion of the barrier reduces the ease of contact between the connected second and third digits and the first digit (thumb).

BRIEF DESCRIPTION OF THE DRAWINGS

FIG. 3 is a perspective view of an insert placed in a glove according to the invention.

FIG. 4 is a front elevation view of the insert shown in FIG. 3.

FIG. 5 is an end view of the insert shown in FIG. 3.

DETAILED DESCRIPTION OF THE INVENTION

Figure 1:
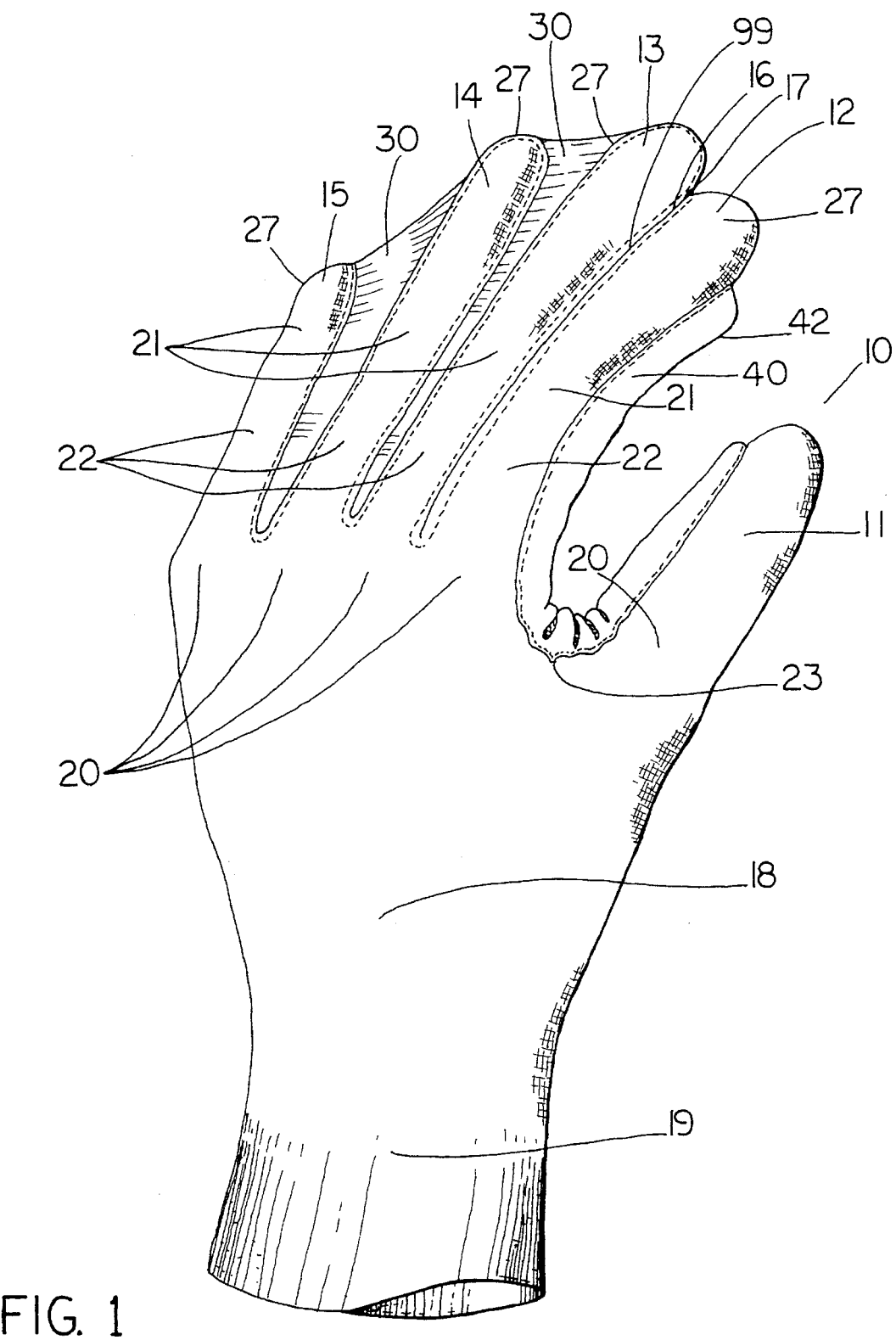
FIG. 1 is a schematic dorsal view of a glove according to the invention.

Although a particular form of apparatus and method has been selected for illustration in the drawings, and although specific terms will be used in the specification for the sake of clarity in describing the apparatus and method steps shown, the scope of this invention is defined in the appended claims and is not intended to be limited either by the drawings selected or the terms used in the specification or abstract. In particular, the detailed description of the best mode of the invention focuses on use of the device and method of the invention for smoking cessation. However, it is to be understood that the invention encompasses such a barrier device and method of its use for treatment of other hand-involved habits, including but not limited to hair-twirling, nail-biting, nose-picking, skin-pulling and scratching, and the like.

The therapeutic device according to the invention includes a barrier preventing contact of a patient's hand with an article which, upon contact with the hand, gives the patient a perceived sense of satisfaction or relief form perceived or subconscious anxiety/tension. In the case of a smoker, the article comprises cigarettes, cigars, or pipes. In other habits the article comprises the hair, nose, mouth, skin, etc. Preferably, the barrier is in the form of a glove 10 worn by the patient and is shown in FIGS. 1 and 2 of the drawings.

Figure 2:
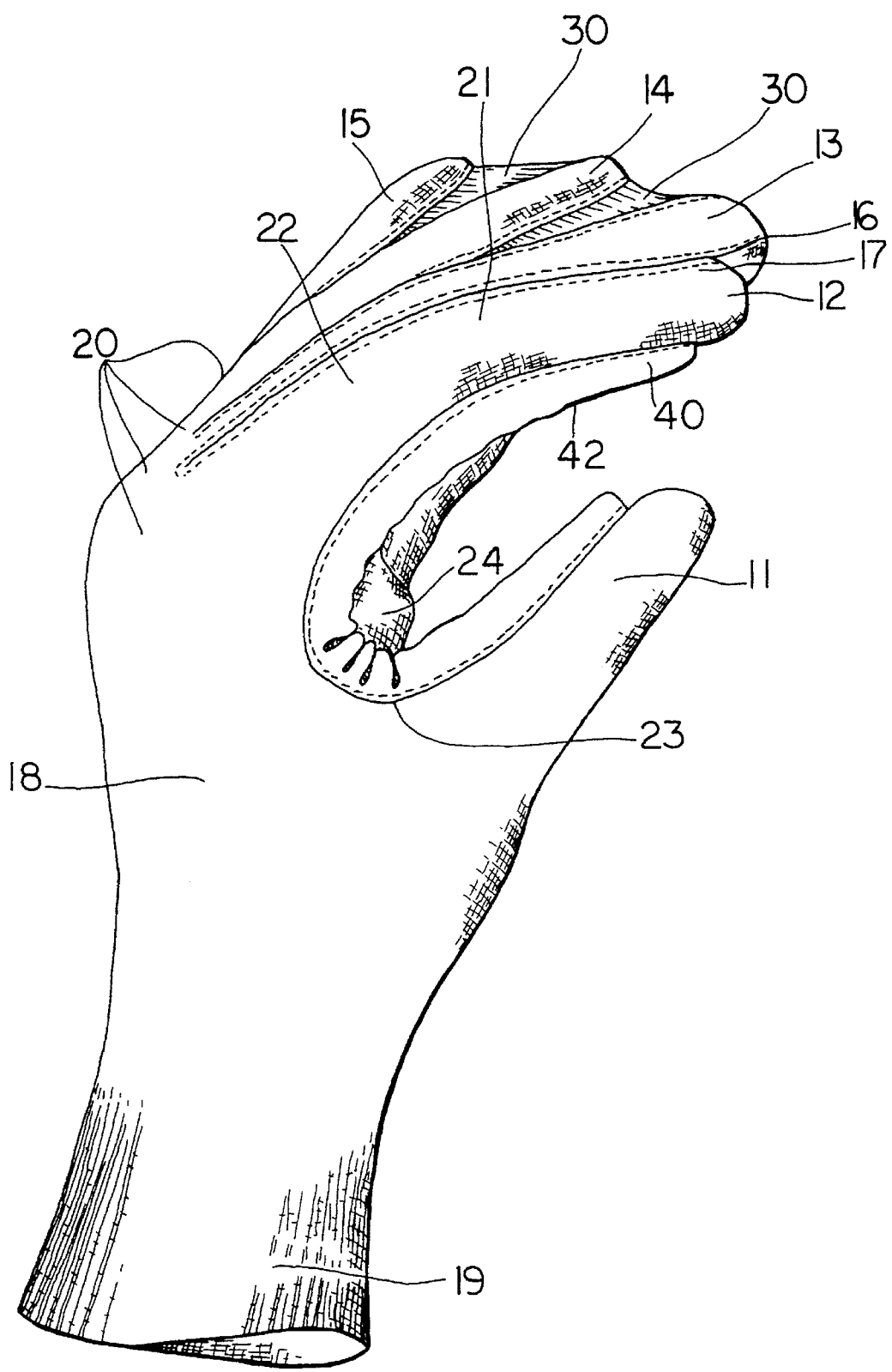
FIG. 2 is a schematic lateral view of a glove according to the invention.

As illustrated in FIGS. 1 and 2, barrier glove 10 contains sleeves for the wearer's first digit (thumb) 11, second digit (pointer finger) 12, third digit (middle finger) 13, fourth digit (ring finger) 14, and fifth digit (pinky finger) 15. The glove further comprises a dorsal portion 18 covering the dorsal portion of the hand (not shown) and the palmar portion 24 of the hand. An optional wristband 19 may be included to maintain barrier glove 10 in place on the hand, but is not critical to the invention as the barrier is preferably produced from a form-fitting material.

Each of the digit sleeves, 11, 12, 13, 14, and 15 connect to and are continuous with the dorsal portion 18 and palmar portion 24 of the glove. Each of the digit sleeves has a distal portion 27 to the dorsal portion 18 and palmar portion 24 at the fingertips of the glove. Digit sleeves connect to dorsal portion 18 and palmar portion 24 at interdigit spaces 25 at their respective ends opposing distal portions 27.

The sleeves for the digits cover all finger, thumb and hand joints of the glove wearer. The sleeves for the digits are preferably continuous. However, joints may be uncovered, particularly on fourth digit 14 and fifth digit 15 for comfort, if necessary. The joints covered in the glove as illustrated in FIGS. 1 and 2, starting at the proximal end of the digits and proceeding towards the distal end are the metacarpalphanlageal (MCP) joints 20, the proximal interphalangeal (PIP) joints 22 and distal interphalangeal (DIP) joints 21.

The sleeve 12 for the second digit is connected to sleeve 13 for the third digit along the medial aspect 17 of the second digit and the lateral aspect 16 of the third digit. This connection serves to substantially reduce independent movement of the second and third digits. Blocking material 30 is placed between the third and fourth digits and between the fourth and fifth digits. Sleeve 42 connects between thumb 11 and second digit 12 and contains insert 40 which restricts ease of opposition of thumb 11 and second digit 12.

Barrier glove 10 can be produced of any material. Preferably the material is one which is form-fitting with the hand of the patient, yet moves freely with and in response to hand motions when the glove is worn. For user comfort, the barrier glove 10 should allow sufficient moisture transfer to prevent the patient's hand from becoming "clammy" from heat and perspiration accumulation. Fabrics such as lycra, cotton spandex and the like are preferably used.

Figure 7:
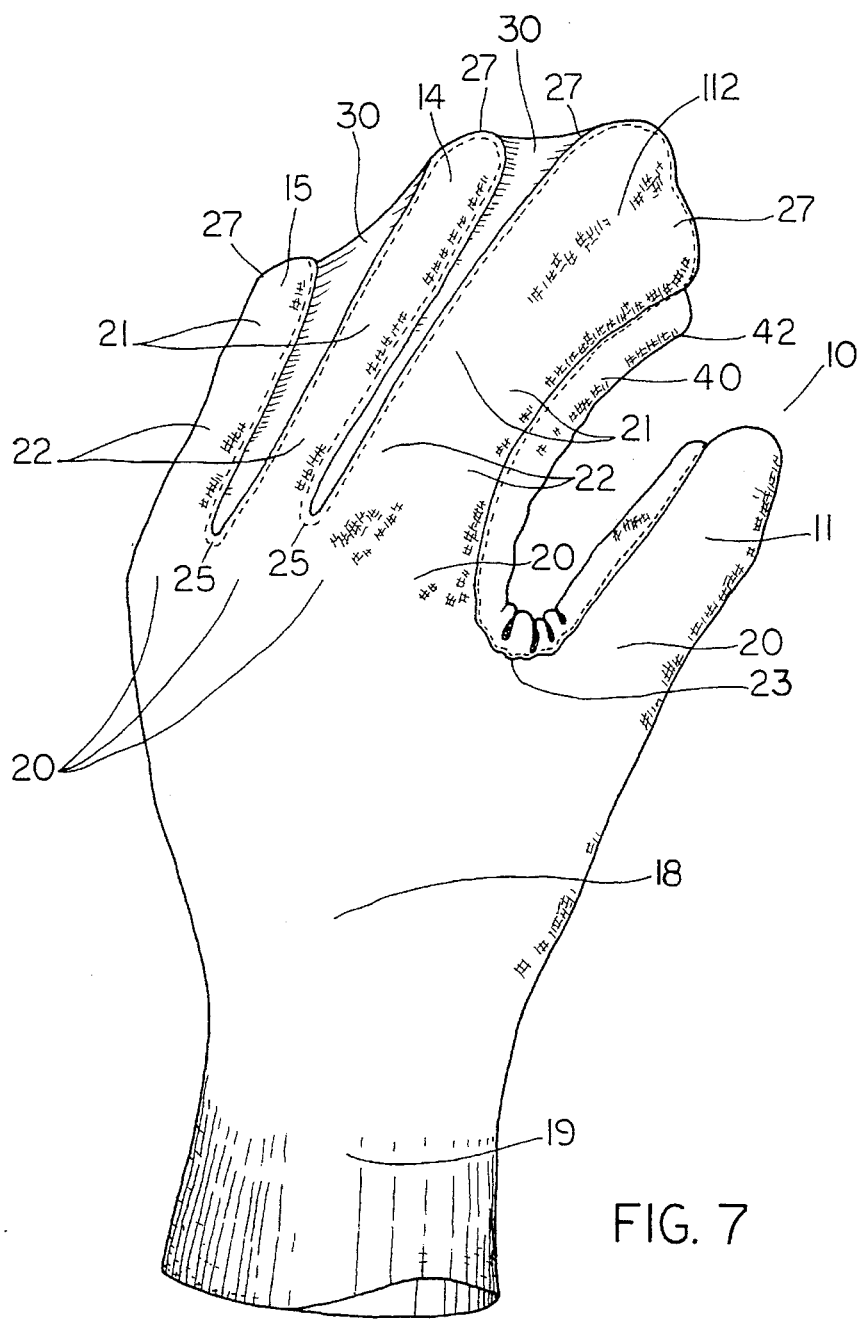
FIG. 7 is another dorsal view of a glove according to the invention.

Preferably, the entire medial side 17 of the second digit 12 is attached directly to the lateral side 16 of the third digit 12 along the palmar and dorsal aspects. The attachment can be by any means such as sewing with threads 99, adhesive, velcro or the like. Preferably, the attachment is unable to be released while the glove is worn, thereby preventing a cigarette from being held between these fingers. This construction allows digits 12 and 13 to each move no more than 10° medially or laterally (abduction or adduction in the plane of the hand). However, because the second and third digits 12, 13 are effectively "buddied" together, and because insert 40 restricts the degree of flexion of second digit 12 at all three joints (DIP 21, PIP 22, and metacarpalphanlageal, MCP 20), both the second and the third digits have limited range of flexion and thus limited opposition to the first digit 11 (thumb) for grasping a cigarette. An alternative manner of reducing medial and lateral movement of second digit 12 and third digit 13 comprises placing these two digits in a single sleeve 112 of the barrier glove 10 as shown in FIG. 7.

Blocking material 30 is connected, such as by sewing, between third and fourth digits 13, 14, and between fourth and fifth digits 14, 15, from inter-digit spaces 25 to distal portions 27 of each digit, to prevent insertion of a cigarette in these spaces, while allowing substantially free motion of the digits in all planes. Preferably blocking material 30 is a web-like or sheet-like material.

Ordinarily a smoker does not utilize positions between third digit 13 and fourth digit 14 and between fourth digit 14 and fifth digit 15 because of the lack of strength and coordination of digits 14 and 15. However, as a result of the construction described earlier between the second and third digits 12, 13, they could become functional for smoking. Blocking material 30 prevents cigarette insertion.

An integral component of barrier glove 10 when utilized to help a patient stop smoking is insert 40 designed to significantly retard grasping a cigarette between thumb 11 and second digit 12 (or between thumb, second and third digits 11, 12, 13, in the "pincer grasp"). Insert 40 is not critical to barrier glove 10 when treating other hand-involved habits. Insert 40 is preferably held inside a sleeve 42. Sleeve 42 is attached securely to barrier glove 10 by sewing, adhesive or the like from an area on the palmar aspect of the second digit distal to the DIP 21, along cradle 23 between thumb 11 and second digit 12 to the medial side of thumb 11, just distal to the interphalangeal joint 22 of thumb 11. Preferably, sleeve 42 is completely enclosed preventing removal of insert 40. Sleeve 42 can be made of the same or a different, preferably less stretchable, material as the remainder of barrier glove 10.

Figure 6:
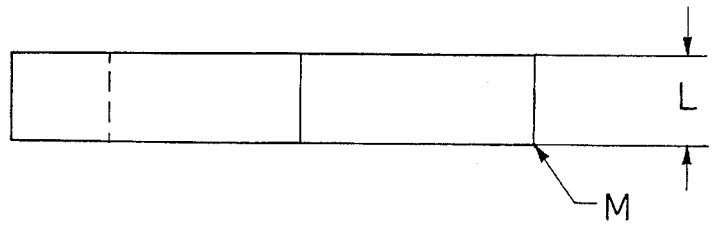
FIG. 6 is a top plan view of the insert shown in FIG. 3.

Insert 40, as shown in FIG. 3, comprises a generally U-shaped article placed between thumb 11 and second digit 12. FIG. 3 provides a perspective view of a preferred embodiment of insert 40, while FIGS. 4, 5, and 6 provide views of insert 40 from the lateral position, the palmar position with the digits in flexion and the top, respectively. The two prongs 43, 44 of the general U-shape of insert 40 rest along the thumb (thumb prong 43) and second digit (second digit prong 44) when in use. The two prongs 43, 44 are joined in a continuous curved portion 45 which rests in cradle 23 between thumb 11 and second digit 12 when in use.

The two prongs 43, 44 and curved portion 45 form a generally continuous outer edge 46 (which rests against the thumb and second digit when in use) and a generally continuous inner edge 47. Inner and outer edges 46, 47 join together at the ends 51, 52 of thumb prong 51 and second digit prong 52. Ends 51 and 52 are tapered in thickness to minimize potential interference of the glove with non-smoking activities which require finger and hand motions. The radii of the outer (rounded) edges of ends 51 and 52 from both the palmar and medial perspectives provide smooth corner transitions to prevent catching of insert 40 or barrier glove 10 on corners of surfaces and rectangular objects encountered in the course of every-day activities and to prevent insert 40 from damaging sleeve 42.

Preferably, thumb prong 43 is generally straight when viewed from the lateral position (FIG. 4). The second digit prong 44 is generally curved inwardly, towards thumb prong 43 when viewed from the lateral position. The end 52 of second digit prong 44 is more distant from curved portion 45 than is end 51 of thumb prong 43, as second digit prong 44 has a greater overall length than thumb prong 43.

Inner edge 47 is generally flat along the plane of the edge, whereas outer edge 46 preferably has a concave surface 98 when viewed from both the dorsal and thumb views. This concave surface 98 allows insert 40 to rest snugly against thumb 11 and second digit 12 which have generally rounded outer surfaces.

The following illustrative dimensions, as indicated in FIGS. 4, 5 and 6, allow insert 40 to accommodate 95% of male human hands:

TABLE 1

| | | |
|---|---|---|
| A | overall length of thumb prong | 1.875 in. |
| B | overall length of second digit prong | 3.433 in. |
| C | overall height of thumb prong | .300 in. |
| D | overall height of insert | 1.500 in. |
| E | angle of inner edge of thumb prong | 5.0° |
| F | angle of inner edge of second digit prong | 10.0° |
| G | angle of outer edge of second digit prong | 17.0° |
| H | radius of curvature, outer edge of second digit prong | 2.750 in. |
| I | radius of curvature, outer edge of curved portion | .625 in. |
| J | radius of curvature, second digit prong lateral view | .080 in. |
| K | radius of curvature thumb prong lateral view | .090 in. |
| L | overall thickness of insert | .562 in. |
| M | radius of curvature end corner, thumb and second digits prong | .030 in. |
| N | radius of curvature inner edge palmar view | .125 in. |
| P | radius of curvature curved surface | 1.50 in |

With these dimensions insert 40 will function in either a left-handed or a right-handed barrier glove.

Most preferably insert 40 is injection molded with a polymeric material such as Exxon Escorene 9074 MED polypropylene polymer, for example. This material allows a reasonable amount of flex, while providing the desired amount of resistance against the pinch motion and retaining sufficient rigidity to ensure reliable "memory" (i.e., returns each time to the same neutral position after force is removed). Alternate materials, such as other polymers, metals, ceramics, wood or aggregates, could be used to provide a range of resistances to the glove, if desired.

An individual motivated to quit smoking puts on one, or a pair, of gloves 10 during the course of normal activities when smoking would occur. By simply wearing barrier glove(s) 10, its deterrent function is achieved by at least the following postulated mechanisms:

(a) Barrier glove(s) 10 on the hand(s) provides the individual with a constant, physical reminder about the need to abstain from smoking, while permitting the individual to perform most other normal activities with the hands.

(b) Barrier glove 10 prevents the individual from holding and manipulating a cigarette in a comfortable or stable position, thus retarding perceived satisfaction from the manual and oral components of smoking and thereby removing these enjoyable, reinforcing aspects of smoking behavior. Webbing 10 prevents insertion of cigarettes between second and third digits 12, 13. Insert 40 contributes to function a) by reducing the possibility of other smoking associated behavior. With insert 40 in its unstressed, neutral position, the person's hand rests in the anatomically "neutral" position. Insert 40 severely limits motion of second and third digits 12, 13. Flexion of second digit 12 at DIP joint 21 and PIP joint 22 is designed to be substantially zero. The MCP joint 20 of second digit 12 can be flexed to approximately 45 degrees with significant resistance. Similarly, flexion of thumb 11 is reduced, particularly palmar flexion (adduction). The presence of insert 40 makes the act of opposition of thumb 11 to second digit 12 and third digit 13 (pulp pinch and three-point pinch) sufficiently strenuous such that prolonged holding and manipulating of a cigarette is physically difficult, if not impossible.

(c) The discrete interruption between the time the individual perceives the desire to smoke and the actual act of lighting up and smoking provides the individual with an important opportunity to consciously recognize and suppress the urge to smoke. This signal can be enhanced by cue cards which the smoker has prepared in advance, which list the individual's reasons (benefits) for quitting, and identification of an underlying pharmacological and/or psychological desire (craving) to smoke, e.g. anxiety, pleasure reinforcement, boredom. Once the individual successfully masters control over craving for cigarettes, the individual gains confidence in being able to repeat this self-reinforcing positive behavior each time the desire to smoke arises. With progressive control over smoking craving, the individual's likelihood of quitting permanently is increased.

The glove(s) can be worn continuously if desired or during waking hours or for whatever length of time is appropriate. Because the hand remains in the neutral position except during activities requiring active flexion of the joints, there has been no indicator of damage to muscles, ligaments, or tendons of the involved digits resulting from prolonged immobilization.

The same glove can also serve as a deterrent for other unhealthy or socially unacceptable "automatic" behaviors involving the hand, such as hair twirling/trichotillomania, nose-picking, nail-biting, pathological scratching and skin-picking, the glove functions to limit the perceived satisfaction of the tactile sensations of these habits, as well. Such behaviors as listed above and other which do not utilize opposition of the thumb with other digits can effectively be treated with a barrier which does not include insert 40 or other means to reduce ease of opposition. The tactile sensations of these behaviors are reduced absent the opposition reducing means.

Although this invention has been described in connection with specific forms thereof, it should be appreciated that a wide array of equivalents may be substituted for the specific elements shown and described herein without departing from the spirit and scope of this invention as described in the appended claims.

I claim:

1. A method for treating a patient for hand-involved habits comprising:

placing a glove comprising digit sections on said patient's hand and reducing the perceived satisfaction associated with the tactile sensations created by contact between said patient's hand and an object which said patient desires to touch during practice of said hand-involved habit by said patient and placing a means extending along a substantial portion of a surface of an area extending along a first and a second digit, said means reducing ease of opposition between the first and the second digit of said patient's hand on which said glove is placed, said means having structural memory so as to return said means to a neutral position after a force placed thereon is removed.

2. The method of claim 1 further comprising preventing substantial independent movement between second and third digits of said patient.

3. The method of claim 1 further comprising reducing the ability of said patient to place said object between the third and fourth digits and between the fourth and fifth digits by placing blocking material between third and fourth digits of the glove and between fourth and fifth digits of the glove.

4. The method of claim 1 further comprising reducing ease of opposition between the thumb and the second digit, and restricting flexion at the proximal interphalangeal and metacarpalphalangeal joints of the second digit of the hand while the glove is worn by placing an article between the first digit of the glove and the second digit of the glove.

5. A method for treating a patient for hand-involved habits comprising:

placing a glove comprising digit sections on said patient's hand and reducing the perceived satisfaction associated with the tactile sensations created by contact between said patient's hand and an object which said patient desires to touch during practice of said hand-involved habit by said patient, substantially reducing independent movement between second and third digits of said hand when said glove is worn by said patient; reducing the ability of said patient to place an object between the third and a fourth digit of said hand and between the fourth and fifth digits of said hand by placing blocking material between the third and a fourth digit of the glove and between the fourth and a fifth digit of the glove; reducing ease of opposition between a first and the second digit of said patient's hand by placing means, between the first and second digits, said means having structural memory so as to return said means to a neutral position after a force placed thereon is removed, and restricting flexion at the proximal interphalangeal and metacarpalphalangeal joints of the second digit of the hand while the glove is worn by placing an article between the first digit of the glove and the second digit of the glove.

6. The method of claim 1 wherein said hand-involved habit is selected from the group consisting of smoking, hair-pulling, nose-picking, nail-biting, scratching and skin-pulling.

7. The method of claim 5 wherein said hand-involved habit is selected from the group consisting of smoking, hair-pulling, nose-picking, nail-biting, scratching and skin-pulling.

8. A device for treating hand-involved habits comprising:
a glove, said glove comprising five digit sections, said digit sections reducing the perceived satisfaction a user of said device associates with tactile sensations created by said user touching an article desired to be touched when said user practices said hand-involved habit;
means for reducing substantial independent movement between second and third digits of said glove;
blocking material located between a third and a fourth digit of said glove;
blocking material located between a fourth and a fifth digit of said glove;
means for reducing the ease of opposition between a first digit and the second digit of said glove, said means having structural memory so as to return said means to a neutral position after a force placed thereon is removed and restricting flexion at proximal interphalangeal and metacarpalphalangeal joints of the second digit of said glove.

9. The glove of claim 8 wherein the second and third digit sections of said glove comprise a single sleeve into which both second and third fingers of a person wearing said glove are placed.

10. The glove of claim 8 wherein said means for reducing substantial independent movement between the second and the third digits comprises sleeves for each of the second and third digits of said glove, attached to each other along the medial aspect of the second digit and the lateral aspect of the third digit.

11. The glove of claim 10 wherein said sleeves are attached by sewing said sleeves together along the medial aspect of the second digit and the lateral aspect of the third digit.

12. The glove of claim 8 wherein said means for reducing the ease of opposition between said first and second digits comprises a generally U-shaped restrictor placed in said glove at a position between the first and second digits.

13. Apparatus for treating a patient who practices habits involving a hand, said apparatus comprising a barrier applied to said hand, said barrier reducing the perceived satisfaction associated with the tactile sensations created by contact between said hand and an object which said patient desires to touch during practice of said habit by said patient; said barrier further comprising means for restricting ease of opposition between a first digit and the second digit of said glove, said means having structural memory so as to return said means to a neutral position after a force placed thereon is removed.

14. The apparatus of claim 13 wherein said barrier comprises a glove placed on the hand of the patient.

15. The apparatus of claim 14 wherein said glove further comprises means for reducing substantial independent movement between a second digit and a third digit of said patient.

16. The apparatus of claim 14 wherein said glove further comprises blocking material connected between a third and a fourth digit and connected between a fourth and a fifth digit.

17. Apparatus for treating a patient who practices habits involving a hand comprising a glove wherein said glove comprises five digit sections and means for reducing substantial independent movement between a second digit and a third digit of the glove by said patient; blocking material connected between the third and a fourth digit of the glove and connected between the fourth and a fifth digit of the glove; and means for reducing ease of opposition between a first digit and the second digit of the glove, and for restricting flexion at proximal interphalangeal and metacarpalphalangeal joints of the second digit; wherein said ease of opposition reducing and movement restricting means comprise a substantially U-shaped article positioned between the first digit of the glove and the second digit of the glove, wherein first and second prongs of the U-shaped article join in a continuous curved portion to form a continuous outer edge and a continuous inner edge; said inner and outer edges joining together at an end portion of each prong, said ends being tapered in thickness; said inner edge having a substantially flat surface and said outer edge having a concave surface; and said first prong is substantially straight and said second prong is curved inwardly towards said first prong, said second prong having a greater overall length than said first prong.

18. Apparatus for treating a patient who practices habits involving a hand, said apparatus comprising a barrier applied to said hand, said barrier reducing the tactile sensations created by contact between said hand and an object which said patient desires to touch during practice of said hand-involved habit by said patient, and said barrier further comprising means for restricting ease of opposition between a first digit and the second digit of said glove, said means having structural memory so as to return said means to a neutral position after a force placed thereon is removed, wherein said hand-involved habit is selected from the group consisting of smoking, hair-pulling, nose-picking, nail-biting, scratching and skin-pulling.

19. The apparatus of claim 17 wherein said hand-involved habit is selected from the group consisting of smoking, hair-pulling, nose-picking, nail-biting, scratching and skin-pulling.

20. A glove comprising:
means for reducing substantial independent movement between second and third digits of said glove;
blocking material located between the third and a fourth digit of said glove;

blocking material located between the fourth and a fifth digit of said glove;

means for reducing the ease of opposition between a first digit of said glove and the second digit of said glove; and means for restricting flexion at proximal interphalangeal and metacarpalphalangeal joints of the second digit of said glove;

wherein said means for reducing the ease of opposition between said first and second digits comprises a generally U-shaped restrictor placed in said glove at a position between the first and second digits;

wherein said generally U-shaped restrictor comprises: first and second prongs joined in a continuous curved portion to form a generally continuous outer edge and a generally continuous inner edge; said inner and outer edges joined together at an end of each prong, said ends being tapered in thickness; said inner edge having a substantially flat surface and said outer edge having a concave surface; and said first prong being substantially straight and said second prong being substantially curved inwardly towards said first prong, said second prong having a greater overall length than said first prong.

* * * * *